(12) United States Patent
Amanullah et al.

(10) Patent No.: US 11,841,303 B2
(45) Date of Patent: Dec. 12, 2023

(54) SIMULATING FLUID LOSS THROUGH DIVERGING FRACTURE FRONTS

(71) Applicant: Saudi Arabian Oil Company, Dhahran (SA)

(72) Inventors: Md Amanullah, Dhahran (SA); Raed A. Alouhali, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 1339 days.

(21) Appl. No.: 16/152,167

(22) Filed: Oct. 4, 2018

(65) Prior Publication Data
US 2020/0110014 A1    Apr. 9, 2020

(51) Int. Cl.
*G01N 11/04* (2006.01)
*G01N 11/02* (2006.01)
*E21B 43/26* (2006.01)
*G01N 11/06* (2006.01)
*E21B 21/00* (2006.01)

(52) U.S. Cl.
CPC ............. *G01N 11/04* (2013.01); *E21B 43/26* (2013.01); *G01N 11/02* (2013.01); *G01N 11/06* (2013.01); *E21B 21/003* (2013.01); *Y10T 137/86212* (2015.04)

(58) Field of Classification Search
CPC ....... Y10T 137/87684; Y10T 137/0329; Y10T 137/2224; Y10T 137/86228; Y10T 137/86212; G01N 11/02; G01N 15/082; G01N 33/2823; G01N 11/04; G01N 11/06; E21B 21/003; E21B 43/26
See application file for complete search history.

(56) References Cited

U.S. PATENT DOCUMENTS 4,340,858 A    7/1982  Malloy
4,472,882 A    9/1984  Hutter
(Continued)

FOREIGN PATENT DOCUMENTS

EP    2749880        7/2014
WO    2009/029451    3/2009
WO    2013/170055    11/2013

OTHER PUBLICATIONS

GCC Examination Report in Gulf Cooperation Council Appln. No. GC 2019-38406, dated Apr. 26, 2021, 3 pages.
(Continued)

*Primary Examiner* — Atif H Chaudry
(74) *Attorney, Agent, or Firm* — Fish & Richardson P.C.

(57) ABSTRACT

An apparatus for simulating fluid loss through diverging fracture fronts includes a housing including an inlet and an outlet. The housing defines an inner volume. The housing can receive and sealingly retain fluid in the inner volume. The housing includes a plate defining an opening formed in an axial surface of the plate. The opening spans a longitudinal thickness of the plate and diverges in dimension along the longitudinal thickness of the plate. The plate is sealingly positioned within the inner volume of the housing between the inlet and the outlet to permit fluid flow from the inlet to the outlet through the opening and to prevent the fluid flow past a circumferential surface of the plate. The apparatus includes a fluidic pressure source fluidically coupled to the housing and configured to flow the fluid through the housing.

20 Claims, 3 Drawing Sheets

(56) References Cited

U.S. PATENT DOCUMENTS

| | | | |
|---|---|---|---|
| 5,602,341 | A | 2/1997 | Lee |
| 8,043,997 | B2 | 10/2011 | Whitfill et al. |
| 2012/0111434 | A1* | 5/2012 | Cadeau ............... F23N 1/007 137/597 |
| 2014/0102188 | A1 | 4/2014 | Murphy et al. |
| 2016/0061701 | A1 | 3/2016 | Amanullah et al. |
| 2016/0178069 | A1* | 6/2016 | Cler ................ G05D 16/2066 137/565.11 |

OTHER PUBLICATIONS

Ofite, "Permeability Plugging Tester—P.P.T. 2,000 PSI (13,800 kPa)—500 Degrees F (260 Degrees C), Part No. 171-90 (115V) Part No. 171-90-01 (230V) Instruction Manual," Version 3.0, OFI Testing Equipment, Inc., Jan. 4, 2017, 22 pages.

Alsaba, "Investigation of lost circulation materials impact on fracture gradient," dissertation in partial fulfillment of the requirements for the degree of Doctor of Philosophy in Petroleum Engineering, Missouri University of Science and Technology, Fall 2015, 184 pages.

Alsaba, "Lost Circulation Materials Capability of Sealing Wide Fractures," SPE-170285-MS, presented at the SPE Deepwater Drilling and Completions Conference, Sep. 10-11, 2014, 12 pages.

Jeennakorn, "The effect of testing conditions on lost circulation materials' performance in simulated fractures," dissertation in partial fulfillment of the requirements for the degree of Doctor of Philosophy in Petroleum Engineering at Missouri University of Science and Technology, Summer 2017, 136 pages.

Hinkebein et al., "Static Slot Testing of Conventional Lost Circulation Materials," Sandia Report, Sand82-180, Unlimited Release, UC-66c, SF 2900-Q(6-82), Jan. 1983, 50 pages.

International Search Report and Written Opinion issued in International Application No. PCT/US2019/054675 dated Feb. 11, 2020, 13 pages.

* cited by examiner

SIMULATING FLUID LOSS THROUGH DIVERGING FRACTURE FRONTS

TECHNICAL FIELD

This specification relates to laboratory equipment to simulate flow through hydrocarbon-carrying formations and through wellbores drilled in such formations.

BACKGROUND

Hydrocarbons entrapped in formations can be recovered by forming wellbores in the formations and producing the hydrocarbons through the wellbores. Forming a wellbore through a formation involves drilling into the formation from a surface of the formation to a desired depth. For example, a drill bit attached to an end of a drill string can be rotated to drill through the formation, thereby forming the wellbore. During drilling, a drilling fluid can be circulated from the surface through the drill string and ports formed in the drill bit. The drilling fluid can return to the surface through an annulus formed between the drill string and an inner wall of the wellbore. The drilling fluid serves several functions including, for example, cooling the drill bit, carrying debris (called cuttings) out of the wellbore, providing weight on bit, among others.

The formation can have fractures, that is, cracks that can extend from the wall of the wellbore into the formation. In some instances, the drilling fluid flowing through the annulus to the surface can flow into the fractures and be lost. Portions of the formation into which the drilling fluid is lost are called loss circulation zones or loss zones.

SUMMARY

This specification describes technologies relating to simulating fluid loss through diverging fracture fronts.

Certain aspects of the subject matter described here can be implemented as a laboratory test apparatus. The apparatus includes a housing including an inlet and an outlet. The housing defines an inner volume. The housing can receive and sealingly retain fluid in the inner volume. The housing includes a plate defining an opening formed in an axial surface of the plate. The opening spans a longitudinal thickness of the plate and diverges in dimension along the longitudinal thickness of the plate. The plate is sealingly positioned within the inner volume of the housing between the inlet and the outlet to permit fluid flow from the inlet to the outlet through the opening and to prevent the fluid flow past a circumferential surface of the plate. The apparatus includes a fluidic pressure source fluidically coupled to the housing and configured to flow the fluid through the housing.

Aspects of the disclosure taken alone or combinable with any of the other aspects can include the following features. The plate has a first end surface nearer the inlet than the outlet and a second end surface nearer the outlet than the inlet. A dimension of the opening at the first end surface is less than a dimension of the opening at the second end surface.

Aspects of the disclosure taken alone or combinable with any of the other aspects can include the following features. A dimension of the opening diverges uniformly from the first end surface to the second end surface.

Aspects of the disclosure taken alone or combinable with any of the other aspects can include the following features. A dimension of the opening diverges non-uniformly from the first end surface to the second end surface.

Aspects of the disclosure taken alone or combinable with any of the other aspects can include the following features. An inner surface of the plate that defines the opening is substantially smooth.

Aspects of the disclosure taken alone or combinable with any of the other aspects can include the following features. An inner surface of the plate that defines the opening is substantially planar.

Aspects of the disclosure taken alone or combinable with any of the other aspects can include the following features. The opening is a first opening. The plate defines multiple openings including the first opening. The multiple openings are spaced apart from each other on the axial surface of the plate. Each opening is spaced apart from each other on the axial surface of the plate. Each opening spans the longitudinal thickness of the plate and diverges in dimension along the longitudinal thickness of the plate.

Aspects of the disclosure taken alone or combinable with any of the other aspects can include the following features. A respective dimension of each opening at the first end surface is less than a respective dimension of each opening at the second end surface.

Aspects of the disclosure taken alone or combinable with any of the other aspects can include the following features. The opening at the first end surface is substantially circular and has a diameter of at least 2 millimeters (mm). The opening at the second end surface is substantially circular and has a diameter of at least 6 mm.

Aspects of the disclosure taken alone or combinable with any of the other aspects can include the following features. The housing can sealingly retain the fluid up to a pressure of 2,000 pounds per square inch (psi).

Certain aspects of the subject matter described here can be implemented as a laboratory test apparatus. The apparatus includes a sealed housing defining an inner volume. The housing includes an inlet and an outlet on respective ends of the housing. The apparatus includes a plate defining a diverging opening formed in an axial surface of the plate. The opening spans a longitudinal thickness of the plate. The plate is positioned within the inner volume of the housing between the inlet and the outlet to permit fluid flow from the inlet to the outlet through the opening and prevent the fluid flow between a circumferential surface of the plate and an inner wall of the housing. The apparatus includes a fluidic pressure source fluidically coupled to the housing and configured to flow the fluid through the housing from the inlet through the opening and to the outlet.

Aspects of the disclosure taken alone or combinable with any of the other aspects can include the following features. The plate has a first end surface nearer the inlet than the outlet and a second end surface nearer the outlet than the inlet. A dimension of the opening at the first end surface is less than a dimension of the opening at the second end surface.

Aspects of the disclosure taken alone or combinable with any of the other aspects can include the following features. A dimension of the opening diverges uniformly from the first end surface to the second end surface.

Aspects of the disclosure taken alone or combinable with any of the other aspects can include the following features. A dimension of the opening diverges non-uniformly from the first end surface to the second end surface.

Aspects of the disclosure taken alone or combinable with any of the other aspects can include the following features. An inner surface of the plate that defines the opening is substantially smooth.

Aspects of the disclosure taken alone or combinable with any of the other aspects can include the following features. An inner surface of the plate that defines the opening is substantially planar.

Aspects of the disclosure taken alone or combinable with any of the other aspects can include the following features. The opening is a first opening. The plate defines multiple openings including the first opening. The multiple openings are spaced apart from each other on the axial surface of the plate. Each opening is spaced apart from each other on the axial surface of the plate. Each opening spans the longitudinal thickness of the plate and diverges in dimension along the longitudinal thickness of the plate.

Aspects of the disclosure taken alone or combinable with any of the other aspects can include the following features. A respective dimension of each opening at the first end surface is less than a respective dimension of each opening at the second end surface.

Aspects of the disclosure taken alone or combinable with any of the other aspects can include the following features. The opening at the first end surface is substantially circular and has a diameter of at least 2 millimeters (mm). The opening at the second end surface is substantially circular and has a diameter of at least 6 mm.

Aspects of the disclosure taken alone or combinable with any of the other aspects can include the following features. The housing can sealingly retain the fluid up to a pressure of 2,000 pounds per square inch (psi).

The details of one or more implementations of the subject matter described in this specification are set forth in the accompanying drawings and the description that follows. Other features, aspects, and advantages of the subject matter will become apparent from the description, the drawings, and the claims.

BRIEF DESCRIPTION OF THE DRAWINGS

Each of FIG. 3A

Like reference numbers and designations in the various drawings indicate like elements.

DETAILED DESCRIPTION

Subsurface fractures causing loss of circulation while drilling can have various types of fracture profiles. In one example, the fractures can have a substantially constant width as they extend from the inner wall of the wellbore being drilled into the formation. In another example, the fractures can converge, that is, have a width that decreases away from the inner wall of the wellbore. In a further example, the fractures can diverge, that is, have a width that increases away from the inner wall of the wellbore. Fractures having different fracture profiles can provide different levels of flow resistance along the fracture length during loss circulation material (LCM) treatment. Fractures with converging profiles have the highest resistance to flow of the LCM. Fractures with diverging profiles can have the least resistance to flow of the LCM. Fractures with substantially constant width can have an intermediate resistance to the flow of LCM. Consequently, a converging fracture profile can create a seal or plug inside the fractures due to increasing wedging, jamming, packing, squeezing and filling action away from the inner wall of the wellbore. Conversely, a diverging fracture profile offers highest flow resistance near the inner wall of the wellbore, the flow resistance decreasing away from the inner wall. In some instances, the loss zone can have mixed front fractures, that is, a combination of parallel profile, converging profile and diverging profile in any sequence.

Laboratory apparatuses can be used to simulate the flow of LCM through fracture profiles. The results of the simulation can be used to predict the suitability of LCM products or pills (or both) for effective sealing and blocking of fractures. This specification describes a laboratory apparatus that can be used to simulate the flow of LCM through diverging fracture profiles. As described earlier, the resistance to flow of LCM through a diverging fracture is different from that to flow through a parallel fracture or a converging fracture. Implementations of the apparatus described here can provide information about the suitability of LCM to seal loss zones with diverging fractures. The apparatus described in this specification can maintain stability at operating temperatures as high as 450 degree Fahrenheit (° F.) and overbalance pressures as high as 2,000 pounds per square inch (psi). The apparatus can accommodate platess having various fracture types and sizes to simulate various loss zones including the in-situ stress and temperature.

Figure 1:
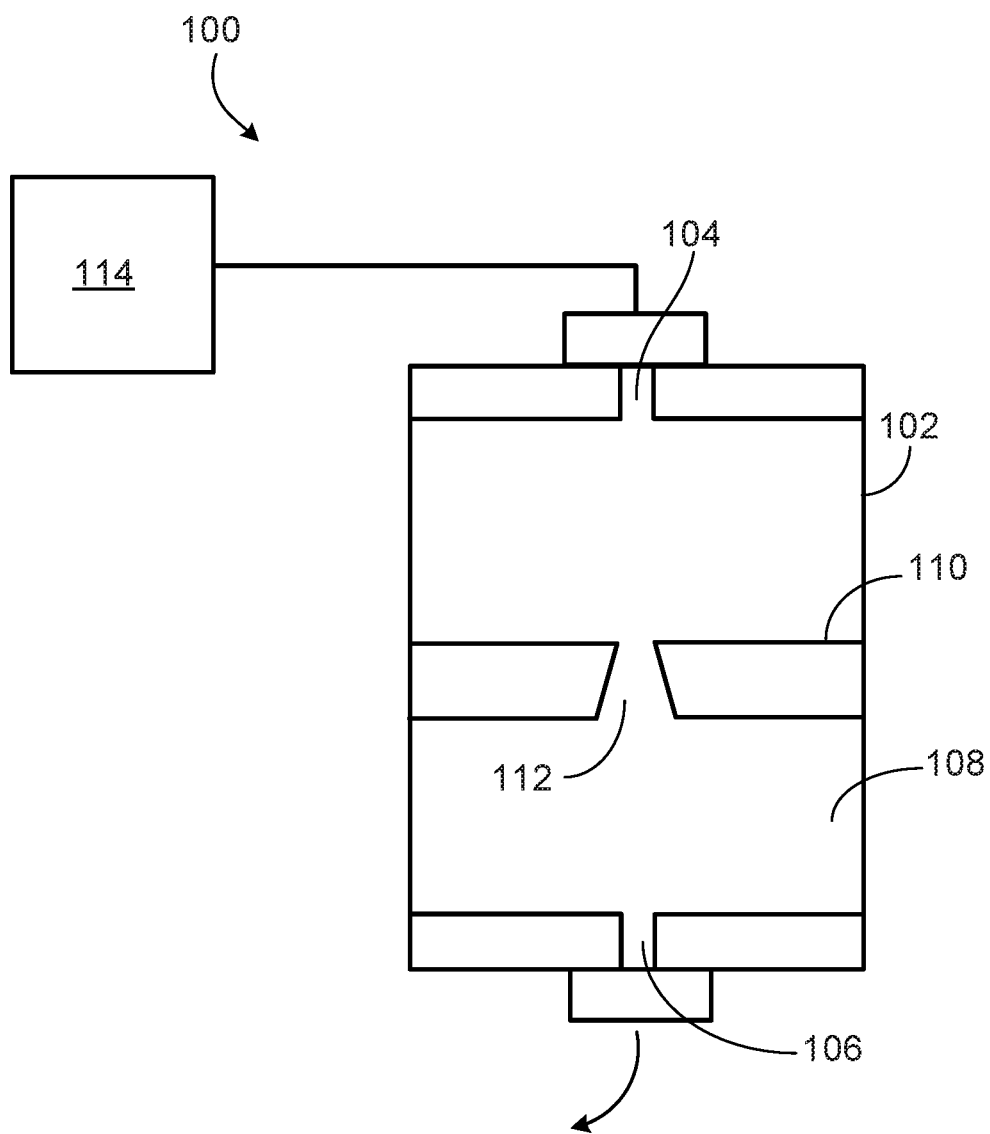
FIG. 1 is a schematic diagram of a laboratory test apparatus.

FIG. 1 is a schematic diagram of a laboratory test apparatus 100. The apparatus 100 can be implemented to test flow of LCM through a diverging fracture profile. The apparatus 100 is dimensioned to be operable in a laboratory. For example, the apparatus 100 can be a bench top apparatus. The apparatus 100 includes a housing 102 having an inlet 104 and an outlet 106. In some implementations, the housing 102 can have a substantially cylindrical interior with a substantially circular cross-section. Other cross-sections for the interior are also possible. The housing 102 defines an inner volume 108. The housing 102 can receive fluid, for example, through the inlet 104 and sealingly retain the fluid in the inner volume 108. That is, after receiving the fluid, the housing 102 can be sealed even if the temperature within the housing 102 is increased to up to 450° F. or the pressure is increased to up to 2,000 psi, or any combination of them. During operation, the apparatus 100 can be oriented such that the inlet 104 and the outlet 106 are above or below one another. In such an orientation, the fluid can flow vertically downward or upward. Alternatively, the apparatus 100 can be oriented such that the fluid can flow horizontally or at a non-zero angle relative to a base on which the apparatus 100 is positioned.

The apparatus 100 includes a plate 110 that defines an opening 112 formed in an axial surface of the plate 110. The opening 112 can be substantially circular and spans a longitudinal thickness of the plate 110 and diverges in dimension along the longitudinal thickness of the plate 110. For example, the opening can have the shape of a truncated cone. Other shapes are also possible for the opening. The plate 110 is sealingly positioned within the inner volume 108 between the inlet 104 and the outlet 106 to permit fluid flow from the inlet 104 to the outlet 106 through the opening and preventing the fluid flow past a circumferential surface of the plate. That is, when the plate 110 is positioned within the inner volume 108, the smaller dimension of the opening 112 is nearer the inlet 104 and the larger dimension of the opening 112 is nearer the outlet 106. When the fluid is flowed from the inlet 104 to the outlet 106, the circumferential surface (that is, the outer surface) of the plate 110 seals against an inner surface of the housing 102 leaving no gap or opening for the fluid to flow past the circumferential surface. Consequently, the fluid necessarily flows through the opening 112 towards the outlet 106.

The apparatus 100 includes a fluidic pressure source 114 fluidically coupled to the housing 102 and configured to flow the fluid through the housing 102. In some implementations, the fluidic pressure source 114 can be a pump that can pump fluid into the housing 102 through the inlet 102. In some implementations, the fluidic pressure source 114 can be a piston assembly with a piston (for example, a floating piston) within the housing 102 that can apply fluidic pressure to the fluid within the housing 102. In some implementations, the fluidic pressure source 114 can be a cylinder of pressurized inert gas (for example, nitrogen or similar inert gas) fitted with a pressure regulator to set the desired test pressure.

Figure 2A:
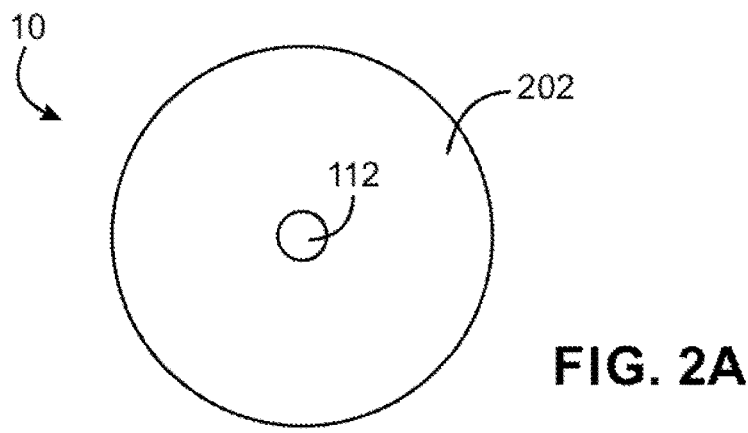
FIGS. 2A-2C are schematic diagrams of a plate used in the apparatus of FIG. 1.
Figure 2B:
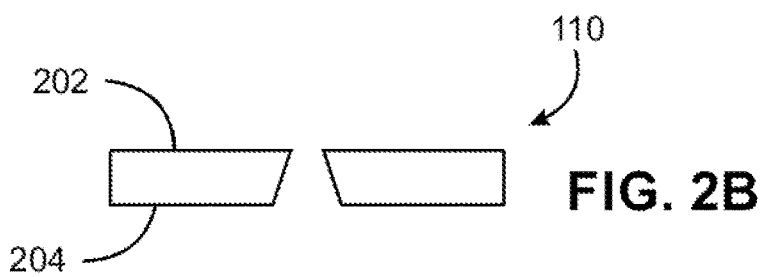
Figure 2C:
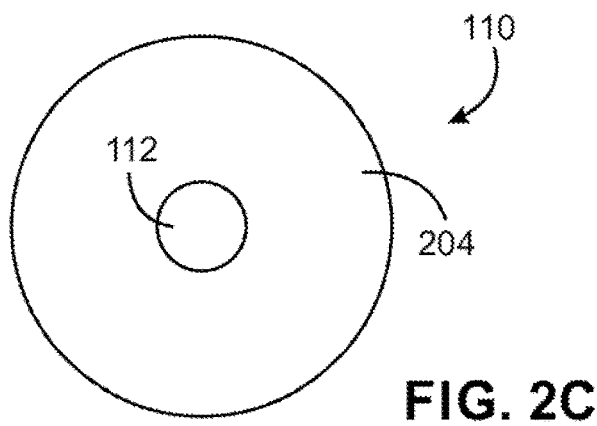
Figure 2D:
FIG. 2D is a schematic diagram of an alternative plate that can be used in the apparatus of FIG. 1.

FIGS. 2A-2C are schematic diagrams of a plate 110 used in the apparatus of FIG. 1. The plate 110 has a first end surface 202 (FIG. 2A, FIG. 2B) that can be nearer the inlet 104 (FIG. 1) and a second end surface 204 (FIG. 2B, 2C) that can be nearer the outlet 106 (FIG. 1). A dimension of the opening 112 at the first end surface 202 is less than a dimension of the opening at the second end surface 204. For example, the opening can be circular in cross-section. The dimension of the opening 112 at the first end surface 202 can be at least 2 millimeters (mm). The dimension of the opening 112 at the second end surface 204 can be greater than 2 mm, for example, 6 mm. The dimensions provided here are examples and variable provided that the dimension at the first end surface 202 is smaller than that at the second end surface. For example, the dimension of the opening 112 at the first end surface 202 can be 1 mm, 2 mm, 3 mm, 4 mm, or 5 mm, and the dimension of the opening 112 at the second end surface 204 can be 3 mm, 4 mm, 5 mm, 6 mm, 7 mm, or 8 mm, respectively, or 9 mm or 10 mm.

In the implementation shown in the schematic diagram of FIG. 2B, the dimension of the opening 112 diverges uniformly from the first end surface 202 to the second end surface 204. That is, an inner surface of the plate 112 that defines the opening 112 is substantially planar. For example, the inner surface is machined to intentionally be as smooth as the machine will allow. Alternatively, a plate 110' that is substantially similar to the plate 110 can be used in the apparatus 100, except that the dimension of the opening 112' defined by the plate 110' diverges non-uniformly from the first end surface to the second end surface of the plate 110'. That is, an inner surface of the plate 112' that defines the opening 112' is intentionally non-planar, for example, includes jagged edges.

Figure 3A:
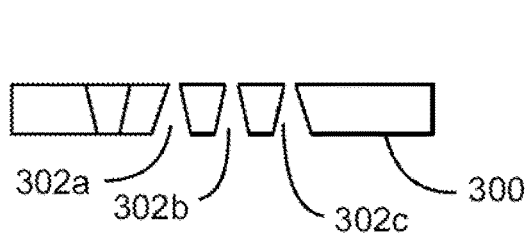
FIG. 3B is a schematic diagram of an alternative plate that can be used in the apparatus of FIG. 1.
Figure 3B:
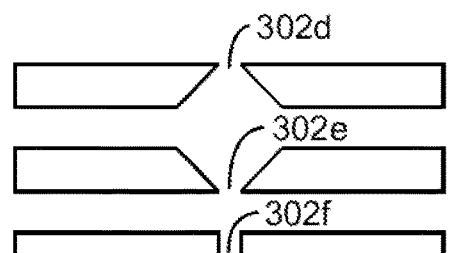

Each of FIG. 3A and FIG. 3B is a schematic diagram of an alternative plate 300 that can be used in the apparatus of FIG. 1. In some implementations, a plate 300 with multiple openings (for example, openings 302a, 302b, 302c) can be used in place of the plate 110 or the plate 110'. The openings can be spaced apart from each other on the axial surface of the plate 300. Like the opening 112 or the opening 112', each opening can span the longitudinal thickness of the plate 300 and diverge in dimension along the longitudinal thickness of the plate 300. All the openings in the plate 300 can be uniform or non-uniform or be a combination of the two.

In some implementations, a modified version of apparatus 100 can accommodate more than one plate along a longitudinal axis of the housing 102. The plates can be stacked one atop the other with no gap in between such that fluid flowing through the opening of one plate flows into the opening of the adjacent plate. In some implementations, at least two plates can be spaced apart. In some implementations, the openings in all the longitudinally spaced plates can have the same diverging opening such as the opening 112 or the opening 112'. In some implementations, the openings in the plates can be a combination of any two or more of diverging openings, converging openings or parallel openings. FIG. 3B is a schematic diagram showing a first plate with a diverging opening 302d stacked atop a second plate with a converging opening 302e stacked atop a third plate with a parallel opening 302f. In some implementations, one or more or all of the longitudinally spaced plates can include multiple openings like the plate 300.

In some implementations, the apparatus 100 can include valves and valve fittings, for example, connected to the inlet 104 and the outlet 106 to permit fluid flow into or out of the sealed housing 102. Seals can be formed where necessary using sealing members (for example, O-rings, metal-to-metal seals or similar seals). The apparatus 100 can include a heating jacket (not shown), for example, surrounding the housing 102 or disposed within the housing 102, to heat the fluid flowed through the housing 102. The apparatus 100 can be connected to or configured to be connected to measuring instruments, for example, pressure gauges, temperature gauges, flow meters, or similar measuring instruments, to measure parameters such as temperature, pressure, flow rate or similar parameters during fluid flow.

Figure 4:
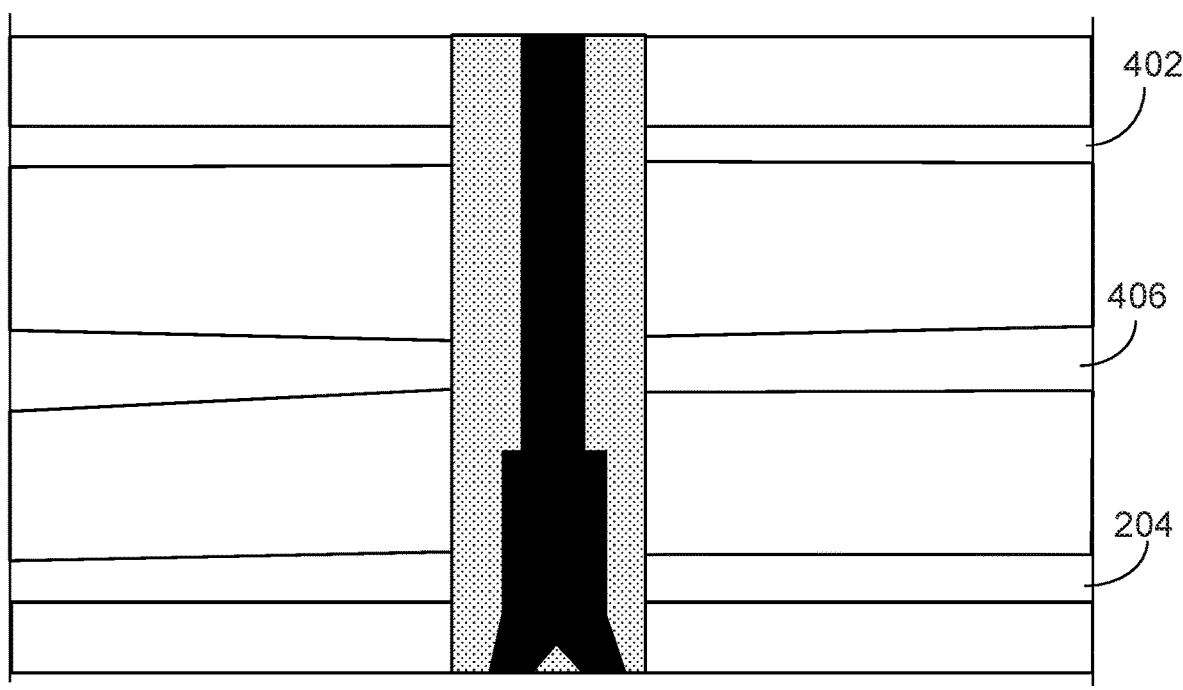
FIG. 4 is a schematic diagram of a wellbore being drilled in a formation having fractures of different gaps.

FIG. 4 is a schematic diagram of a wellbore being drilled in a formation having fractures of different gaps. For example, the fracture 402 is a gap with a substantially parallel profile, the fracture 404 is a gap with a converging profile and the fracture 406 is a gap with a substantially diverging profile. When LCM is flowed through the wellbore to seal the fractures, it is hypothesized that the gap 404 will offer the least resistance to being sealed, the gap 406 will offer the most resistance to being sealed and the gap 402 will offer an intermediate resistance to being sealed. The apparatus 100 can be used to simulate the flow of LCM through such fractures to validate the hypothesis.

Example 1

A LCM blend (LCM Blend-1) composed of 12 parts per billion (ppb) of plastic chips, 12 ppb of granular starch and 4 ppb of fibers was formulated and evaluated using the apparatus 100 and using an apparatus similar to the apparatus 100 except with a plate having parallel openings. The test parameters for the two apparatuses were identical. Table 2 shows certain fluid flow parameters measured using the two different apparatuses.

TABLE 2

| LCM Blend | Test Fixture | Spurt Loss (cc) | Fluid loss (cc) | Total Leak-off (cc) | Cake Thickness (mm) |
|---|---|---|---|---|---|
| LCM Blend-1 | Apparatus with parallel gap profile plate | 0.5 | 0 | 0 | 1 |

TABLE 2-continued

| LCM Blend | Test Fixture | Spurt Loss (cc) | Fluid loss (cc) | Total Leak-off (cc) | Cake Thickness (mm) |
|---|---|---|---|---|---|
| LCM Blend-1 | Apparatus 100 | Total loss | Total Loss | Total Loss | NA |

Thus, the apparatus 100 validates the hypothesis that the resistance to flow of the LCM blend through a diverging front fracture is less compared to the corresponding resistance to flow through a parallel front fracture.

Example 2

A LCM blend (LCM Blend-2) composed of 10 ppb of organic fiber and 10 ppb of granular starch was formulated and evaluated using the apparatus 100 and using an apparatus similar to the apparatus 100 except with a plate having parallel openings. The test parameters for the two apparatuses were identical. Table 3 shows certain fluid flow parameters measured using the two different apparatuses.

TABLE 3

| LCM Blend | Test Fixture | Spurt Loss (cc) | Fluid loss (cc) | Total Leak-off (cc) | Cake Thickness (mm) |
|---|---|---|---|---|---|
| LCM Blend-2 | Apparatus with parallel gap profile plate | 2 | 22 | 22 | NA |
| LCM Blend-2 | Apparatus 100 | 50 | 300 | 350 | NA |

Thus, the apparatus 100 further validates the hypothesis that the resistance to flow of the LCM blend through a diverging front fracture is less compared to the corresponding resistance to flow through a parallel front fracture. The results shown in Tables 2 and 3 reveal that simulating fractures with diverging profiles requires an apparatus such as the apparatus 100 that includes openings with diverging profiles.

Thus, particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results.

The invention claimed is:

1. A laboratory test apparatus comprising:
a housing comprising an inlet and an outlet, the housing defining an inner volume, the housing configured to receive and sealingly retain fluid in the inner volume;
a plurality of plates stacked one atop the other along a longitudinal axis of the housing, each plate defining respective opening formed in respective axial surface of each plate, each opening spanning a longitudinal thickness of each plate, an opening of a first plate of the plurality of plates diverging in dimension along the longitudinal thickness of the first plate, an opening of a second plate of the plurality of plates converging in dimension along the longitudinal thickness of the second plate, an opening of a third plate of the plurality of plates being parallel along the longitudinal thickness of the third plate, each plate sealingly positioned within the inner volume of the housing between the inlet and the outlet to permit fluid flow from the inlet to the outlet through the opening of each of the first plate, the second plate and the third plate and preventing the fluid flow past a circumferential surface of each plate; and
a fluidic pressure source fluidically coupled to the housing and configured to flow the fluid through the housing.

2. The apparatus of claim 1, wherein the first plate has a first end surface nearer the inlet than the outlet and a second end surface nearer the outlet than the inlet, wherein a dimension of the opening of the first plate at the first end surface is less than a dimension of the opening of the first plate at the second end surface.

3. The apparatus of claim 2, wherein a dimension of the opening of the first plate diverges uniformly from the first end surface to the second end surface.

4. The apparatus of claim 2, wherein a dimension of the opening of the first plate diverges non-uniformly from the first end surface to the second end surface.

5. The apparatus of claim 2, wherein an inner surface of the first plate that defines the opening of the first plate is substantially smooth.

6. The apparatus of claim 2, wherein an inner surface of the first plate that defines the opening of the first plate is substantially planar.

7. The apparatus of claim 2, wherein the opening of the first plate is a first opening, wherein the first plate defines a plurality of openings comprising the first opening, the plurality of openings spaced apart from each other on the axial surface of the first plate, each opening spanning the longitudinal thickness of the first plate and diverging in dimension along the longitudinal thickness of the first plate.

8. The apparatus of claim 7, wherein a respective dimension of each opening of the first plate at the first end surface is less than a respective dimension of each opening at the second end surface.

9. The apparatus of claim 2, wherein the opening of the first plate at the first end surface is substantially circular and has a diameter of at least 2 millimeters (mm), wherein the opening of the first plate at the second end surface is substantially circular and has a diameter of at least 6 mm.

10. The apparatus of claim 1, wherein the housing is configured to sealingly retain the fluid up to a pressure of 2,000 pounds per square inch.

11. A laboratory test apparatus comprising:
a sealed housing defining an inner volume, the housing comprising an inlet and an outlet on respective ends of the housing;
a plurality of plates stacked one atop the other along a longitudinal axis of the housing, a first plate of the plurality of plates defining a diverging opening formed in an axial surface of the first plate, a second plate of the plurality of plates defining a converging opening formed in an axial surface of the second plate, a third plate of the plurality of plates defining a parallel opening formed in an axial surface of the third plate, each opening spanning a longitudinal thickness of each plate, each plate positioned within the inner volume of the housing between the inlet and the outlet to permit fluid flow from the inlet to the outlet through the opening of each of the first plate, the second plate and the third plate, and preventing the fluid flow between a circumferential surface of each plate and an inner wall of the housing; and
a fluidic pressure source fluidically coupled to the housing and configured to flow the fluid through the housing from the inlet through the opening and to the outlet.

12. The apparatus of claim 11, wherein the first plate has a first end surface nearer the inlet than the outlet and a second end surface nearer the outlet than the inlet, wherein a dimension of the opening of the first plate at the first end surface is less than a dimension of the opening of the first plate at the second end surface.

13. The apparatus of claim 12, wherein a dimension of the opening of the first plate diverges uniformly from the first end surface to the second end surface.

14. The apparatus of claim 12, wherein a dimension of the opening of the first plate diverges non-uniformly from the first end surface to the second end surface.

15. The apparatus of claim 12, wherein an inner surface of the first plate that defines the opening of the first plate is substantially smooth.

16. The apparatus of claim 12, wherein an inner surface of the first plate that defines the opening of the first plate is substantially planar.

17. The apparatus of claim 12, wherein the opening of the first plate is a first opening, wherein the first plate defines a plurality of openings comprising the first opening, the plurality of openings spaced apart from each other on the axial surface of the first plate, each opening spanning the longitudinal thickness of the plate and diverging in dimension along the longitudinal thickness of the first plate.

18. The apparatus of claim 17, wherein a respective dimension of each opening at the first end surface is less than a respective dimension of each opening at the second end surface.

19. The apparatus of claim 12, wherein the opening of the first plate at the first end surface is substantially circular and has a diameter of at least 2 millimeters (mm), wherein the opening at the second end surface is substantially circular and has a diameter of at least 6 mm.

20. The apparatus of claim 11, wherein the housing is configured to sealingly retain the fluid up to a pressure of 2,000 pounds per square inch.

* * * * *